United States Patent

Vanlerberghe et al.

[11] Patent Number: 4,879,107
[45] Date of Patent: Nov. 7, 1989

[54] FOAMING COSMETIC COMPOSITIONS

[75] Inventors: Guy Vanlerberghe, Claye-Souilly; Henri Sebag, Paris; Michele Lagoutte; Jean F. Grollier, both of Paris, all of France

[73] Assignee: L'Oreal, Paris, France

[21] Appl. No.: 190,052

[22] Filed: May 4, 1988

[30] Foreign Application Priority Data

May 8, 1987 [LU] Luxembourg .............................. 86873

[51] Int. Cl.⁴ ............................................... A61K 7/09
[52] U.S. Cl. .......................................... 424/70; 424/78
[58] Field of Search ....................... 252/8.05, DIG. 13; 424/78, 70; 585/17

[56] References Cited

U.S. PATENT DOCUMENTS 4,138,427 2/1979 Vanlerberghe et al. ... 252/DIG. 13
4,439,329 3/1984 Kleiner et al. ...................... 252/8.05

FOREIGN PATENT DOCUMENTS 2558591 7/1977 Fed. Rep. of Germany .
2530141 1/1984 France .
 476035 7/1969 Switzerland .
2014584 8/1979 United Kingdom .
2144133 2/1985 United Kingdom .

Primary Examiner—Joseph L. Schofer
Assistant Examiner—Jeffrey T. Smith
Attorney, Agent, or Firm—Cushman, Darby & Cushman

[57] ABSTRACT

Foaming cosmetic compositions for cleansing the hair or the skin, containing, in proportions from 0.5 to 95%, a surfactant oligomer of formula (I):

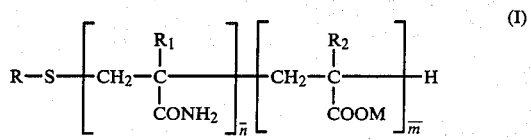

in which:

R denotes a $C_{10}$–$C_{18}$ hydrocarbon radical;
$R_1$ and $R_2$, which may be identical or different, denote H or $CH_3$;
$\bar{n}$ denotes an average statistical value from 10 to 35;
$\bar{m}$ denotes zero or an average statistical value $\leq 5$;
$\bar{m}/\bar{n}$ preferably being $\leq 0.25$
M denotes H, Na, K or an ammonium group.

These compositions are characterized by good foaming power, good compatibility with the skin and the ocular mucosae and a suitable detergent power.

10 Claims, No Drawings

FOAMING COSMETIC COMPOSITIONS

The present invention relates to foaming cosmetic compositions for cleansing the hair and/or the skin, or especially in the form of shampoos, foam baths, shower products and makeup-removal compositions.

Foaming cosmetic compositions must satisfy a number of criteria including, in particular, cleansing power, foaming properties and low irritancy with respect to the skin or the ocular mucosae.

The relative importance of these main criteria varies according to the applications, and can change with fashion or with the lifestyle. Since, moreover, it can be difficult to optimize all the properties at the same time, the frequent outcome is that certain of them are given preference.

Thus, for example, nowadays, with the increased frequency of shampooing and of taking showers and baths, it is chiefly sought to improve the biological properties and the foaming properties rather than the detergent properties.

Foaming compositions for cleansing the hair or the skin, which provide an abundant foam of good quality or which are completely inoffensive to the skin and the mucosae, are known, but there is still a need for foaming cosmetic compositions which produce a foam which is both abundant and of high quality, and which are very inoffensive to the skin and the mucosae, and especially to the ocular mucosae, while providing for sufficient detergency of the hair and of the skin.

The subject of the invention is a foaming cosmetic composition for cleansing the hair and the skin and which is usable as shampoos, as foam baths and shower products, and as makeup-removal solutions for the face and the eyes, characterized in that it contains, as foaming agent, a surfactant oligomer of formula:

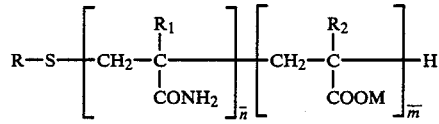

in which:
R denotes a linear $C_{10}$ to $C_{18}$, and preferably $C_{11}$ to $C_{15}$, hydrocarbon radical containing an even or odd number of carbon atoms;
$R_1$ and $R_2$, which may be identical or different, denote a hydrogen atom or a methyl radical;
$\bar{n}$ denotes an average statistical value from 10 to 35 and preferably from 15 to 25;
$\bar{m}$ denotes an average statistical value from zero to 5 and, when $\bar{m}$ is other than zero, the ratio $\bar{m}/\bar{n}$ is preferably lower than or equal to 0.25;
M denotes a hydrogen atom, a sodium or potassium atom or alternatively an ammonium group such as $NH_4$, 2-ammonio-2-methyl-1-propanol, 2-ammonio-2-methyl-1,3-propanediol, trimethylhydroxyethylammonium or triethanolammonium.

The preferred oligomers include those for which R is a $C_{12}$–$C_{18}$ alkyl radical; $\bar{n}$ denotes an average statistical value from 10 to 30; $\bar{m}$ denotes zero or an average statistical value of 5; $R_1$ denotes hydrogen or methyl and $R_2$ denotes methyl.

Especially advantageous are the oligomers for which R denotes a dodecyl radical; $R_1$ denotes hydrogen or methyl; $\bar{n}$ denotes an average statistical value from 10 to 30, and $\bar{m}$ denotes zero; or alternatively oligomers for which R denotes stearyl; $\bar{n}$ denotes an average statistical value of 20; $\bar{m}$ denotes an average statistical value of 5; $R_1$ denotes hydrogen and $R_2$ denotes methyl.

The compounds of formula (I) are oligomers having a molecular weight of between 900 and 3500.

The compound of formula (I) are known.

Thus, in U.S. Pat. No. 4,439,329, the oligomers of formula (I) are included in a very broad family of oligomers which are usable as foam stabilizers for protein-based extinguishers.

Moreover, in German Pat. No. 2,558,591, the use has been described of certain compounds of formula (I) as a dispersant agent in alkaline soaps for producing toilet soaps.

The Applicant has discovered that the oligomers of formula (I) may be used as a foaming agent in soap-free cosmetic compositions.

These products of formula (I) are, in addition, very well tolerated biologically.

The compounds of formula (I) may be prepared by the polymerization of acrylamide or methacrylamide monomer(s) in the presence of a free-radical initiator and of an alkylmercaptan, RSH, as a transfer agent [R having the same meaning as in the formula (I)].

The acrylamide and/or methacrylamide monomers preferably represent at least 80% of the hydrophilic units constituting the surfactants oligomers of the invention. The other possible units, containing the COOM group, are obtained either by the introduction, simultaneously with the acrylamide or with the methacrylamide, of acrylic or methacrylic acid, or of the methyl or ethyl ester of these acids, and saponification; or by the partial hydrolysis of the $CONH_2$ groups of a (meth)acrylamide homopolymer.

The radical initiators which are usable may be chosen from organic peroxides, hydroperoxides, hydrogen peroxide, alkali metal persulphates or azo compounds. The proportions of catalysts used are between 0.05% and 0.5% with respect to the weight of the monomer(s).

The polymerization reactions are generally carried out by solubilization, in a solvent, of the mercaptan RSH and the monomer or monomers, and the gradual introduction, in a nitrogen atmosphere, at a temperature of between 40° and 90° C., of the catalyst solubilized in a solvent such as water, methanol, ethnol or isopropanol, or a mixture of these. The solvents which are usable for the polymerization are generally chosen from methanol, ethanol, isopropanol, a mixture thereof and water.

The molar proportions of monomer(s) with respect to the mercaptan RSH are chosen in accordance with the average values desired for $\bar{n}$ and $\bar{m}$. The surfactant oligomers generally precipitate in the alcoholic solvents used and can thereby be separated and purified in order to remove the remaining monomers. 96° strength ethanol is the preferred solvent for removing the monomer such as acrylamide or methacrylamide. In the case where the solvent is water, the residual monomer or monomers may optionally be separated by dialysis.

It can also be advantageous, in order to consume the final traces of monomers, to add small amounts of products containing at least one thio or amine group capable of reacting with the acrylic group.

Such compounds can be, for example, cysteine, thioethanol, thioglycerol, thioglycolic acid, diethanolamine, diglycolamine, polysulphydryl polymers or primary or secondary polyamines.

The subject of the invention is also foaming cosmetic cleansing compositions, in the form of shampoos, foam baths, shower products or a makeup-removal composition, containing at least one surfactant oligomer of formula (I) in the presence of foam stabilizers and optionally of other surfactants. Other cosmetic adjuvants can also be present.

The object of the invention is also the use of the surfactant oligomers of formula (I) as a foaming base for shampoo compositions, foam bath compositions, and shower products and makeup-removal product compositions, optionally in the presence of foam stabilizers and/or of other surfactants and/or cosmetic adjuvants.

The object of the invention is also a process for cleansing the hair and the skin, characterized in that a sufficient amount of a foaming cleansing composition containing a foaming surfactant of formula (I) is applied on the hair or on the skin.

The surfactant oligomers of the invention can be used in powder or gel form, or in aqueous solution. The concentrations by weight of the surfactant oligomers of formula (I) with respect to the total weight of the composition can vary from 0.5 to 95%, depending on the presentation and the use. Thus, for example, for make-up-removal solutions, the concentration of compounds of formula (I) can vary from 0.5 to 5% by weight.

For shampoo or shower product compositions, the concentration of compounds of formula (I) can vary from 5% to 25% by weight, and, in the case of compositions for foam baths, from 10 to 95% by weight.

In the different compositions according to the invention, the foaming surfactants consist to the extent of at least 40% of the surfactant oligomers of formula (I). The other surfactants present can be either products which are themselves foaming, or additives whose role is to stabilize the foam or to improve its properties.

Among the other foaming products which can be combined with the surfactant oligomers, there may be mentioned, for example, anionic surfactants such as alkyl sulphates, alkyl ether sulphates, alkali metal alkylarylsulphonates or alkanolamines, salts of alkyl polyether carboxylic acids, salts of alkylphenyl polyether carboxylic acids, N-acylamino acids; nonionic surfactants such as alkyl ethers of polyglycerols or of polyethylene glycols, alkyl glucosides; copolymers of ethylene oxide and propylene oxide; polyoxyethylenated $C_{10}$–$C_{18}$ fatty alcohols, polyoxyethylenated $C_{10}$–$C_{18}$ fatty acid esters such as sorbitan monolaurate polyoxyethylenated with 20 moles of ethylene oxide, amphoteric surfactants such as N-alkylamino acids or surfactants of the alkylimidazoline type, betaines containing fatty chains or amidobetaines derived from fatty acids; the fatty chains and the alkyl or acyl radicals of the above compounds containing from 10 to 18 carbon atoms.

Among the foam-stabilizing additives, there may be mentioned chiefly $C_{11}$ to $C_{18}$ alkanediols, glycerol ethers, and fatty alkanolamides derived from mono- or di-ethanolamine or from tris(hydroxymethyl)aminomethane.

The foaming cosmetic compositions according to the invention can take the form of powders, aqueous solutions or aqueous gels.

The aqueous solutions and aqueous gels preferably have an acidic pH of between 3 and 7. The pH is adjusted to this value by adding inorganic or organic acids, or by adding both an organic acid and a base such as sodium hydroxide, potassium hydroxide or alkanolamines, or by adding a base alone.

Among acidifying agents, $C_2$–$C_6$ carboxylic acids, such as acetic, glycolic, lactic, citric, tartaric or gluconic acid, are preferably used.

Among the adjuvants which can be contained in the foaming cosmetic compositions according to the invention, there should be mentioned, more especially, natural and synthetic polymers, thickeners, opacifiers, oils, waxes, proteins, amino acids, preservatives, colourings and perfumes.

The invention is illustrated by the non-limiting examples below.

PREPARATION EXAMPLES

Example I

Preparation of a mixture of compounds of formula (I) in which:
$R = C_{12}H_{25}$
$R_1 = H$
$\bar{n} = 25$ and $\bar{m} = 0$ 10.1 g of dodecylmercaptan (0.05 mole) and 88.8 g of acrylamide (1.25 mole) were solubilized in 400 g of isopropanol. The apparatus was flushed with nitrogen and the reaction mixture heated to 80° C. 25 g of isopropanol containing 0.18 g of azodiisobutyronitrile were then gradually introduced in the course of 3 hours to 3½ hours, still in a nitrogen atmosphere, and at 80° C. Heating and stirring were maintained for 3 to 4 hours after completion of the addition. The product precipitated in the course of the reaction in the form of a finely divided white product. Upon completion of the reaction, the product was filtered off and washed three times with 100 to 200 ml of isopropanol. It was then dried under reduced pressure at 50° C.

100 g of a white water-soluble powder were thus obtained.

The progress of the reaction was followed by titration of the remaining mercaptan in the isopropanol medium and by thin layer chromatography on a silica support with a $CH_2Cl_2/CH_3OH$: 8/2 eluent.

Examples II, III, IV, V, VI

The following products were prepared according to the procedure of Example I:

| Example | R | $R_1$ | n | m |
|---|---|---|---|---|
| II | $C_{12}H_{25}$ | H | 10 | 0 |
| III | $C_{12}H_{25}$ | H | 15 | 0 |
| IV | $C_{12}H_{25}$ | H | 20 | 0 |
| V | $C_{12}H_{25}$ | H | 30 | 0 |
| VI | $C_{12}H_{25}$ | $CH_3$ | 25 | 0 |

The amounts of reactants used were as follows:

| Example | RSH (g) | RSH (mole) | Monomer (a,b) (g) | Monomer (a,b) (mole) | Isopropanol (g) | ADIBN (g) |
|---|---|---|---|---|---|---|
| II | 20.2 | 0.1 | 71(a) | 1 | 365 | 0.07 |
| III | 14.1 | 0.07 | 74.5(a) | 1.05 | 355 | 0.15 |
| IV | 10.1 | 0.05 | 71(a) | 1 | 324 | 0.14 |
| V | 10.1 | 0.05 | 106.5(a) | 1.5 | 465 | 0.21 |
| VI | 10.1 | 0.05 | 106(b) | 1.25 | 465 | 0.2 |

(a): acrylamide
(b): methacrylamide
ADIBN: azodiisobutyronitrile.

Example VII

Preparation of a mixture of surfactant oligomers of formula (I) in which:
$R = C_{12}H_{25}$
$R_1 = H$
$\bar{n} = 25$ and $\bar{m} = 0$ 400 g of methanol were introduced into a 1-liter round-bottomed flask, and 10.1 g of dodecylmercaptan (0.05 mole) and 88.75 g of acrylamide (1.25 mole) were then introduced under a nitrogen stream. The reaction mixture was heated to 50° C. and a solution of 0.44 g of ammonium persulphate in a mixture of 5 ml of water and 15 ml of methanol was introduced dropwise. Duration of the addition: 2 hours 30 minutes.

The mixture was heated for 3 hours and 30 minutes and an equivalent amount of alcholic solution of ammonium persulphate was added agin. Heating was resumed for 5 hours.

The methanol was partially evaporated off under normal pressure and the residual mass (240 g) was taken up with 350 g of isopropanol.

The oligomer precipitate was filtered off and rinsed with isopropanol.

After drying, 99 g of water-soluble powdered white product were thus obtained.

Example VIII

Preparation of a mixture of surfactant oligomers of formula (I) in which:
$R = C_{18}H_{37}$
$R_1 = H$
$R_2 = CH_3$
$M = H$
$\bar{n} = 20$ and $\bar{m} = 5$ 425 g of isopropanol, 14.3 g (0.05 mole) of stearylmercaptan, 71 g of acrylamide (1 mole) and 21.5 g of methacrylic acid (0.25 mole) were introduced under a nitrogen stream into a 2-liter round-bottomed flask, and 0.18 g of azobisisobutyronitrile solubilized in 30 ml of isopropanol was then introduced dropwise, at 80° C., over 3 hours and 45 minutes.

Stirring and heating were maintained, still under nitrogen, for 6 hours.

0.26 g of diethanolamine was then added and heating was resumed for another 5 hours.

The precipitate was filtered off and rinsed twice with 200 ml of isopropanol.

A product was thus obtained in the form a water-soluble white powder.

APPLICATION EXAMPLES

Example 1

| FOAM BATH | |
|---|---|
| Compound of Example I | 12 g |
| Sodium $C_{12}$—$C_{14}$ alkyl ether sulphate oxyethylenated with 2.2 moles of ethylene oxide | 8 g |
| Coconut diethanolamides | 2 g |
| Colorings, preservatives, perfume qs | |
| Triethanolamine | qs pH = 7 |
| Water | qsp 100 g |

Example 2

| FOAM BATH | |
|---|---|
| Compound of Example I | 20 g |
| Copolymer of dimethyldiallyl ammonium chloride and acrylamide, MW > 500,000, sold under the trade name MERQUAT 550 by the MERCK company | 0.3 g |
| Colorings, preservatives, perfume qs | |
| Lactic acid | 0.5 g |
| Triethanolamine qs pH = 5 | |
| Water | qsp 100 g |

Example 3

| SHAMPOO | |
|---|---|
| Compound of Example I | 10 g |
| Polyalkoxycarboxylate sold at a 90% AS concentration under the trade name AKYPO RLM 45 by the CHEM Y company | 12 g AS |
| Ether of hexadecanediol and of polyethyleneglycol (70 ethoxy groups) | 2 g |
| Colorings, preservatives, perfume qs | |
| Triethanolamine qs pH = 7 | |
| Water | qsp 100 g |

AS = active substance.

Example 4

| FOAM BATH | |
|---|---|
| Compound of Example IV | 15 g |
| Alkyl ether of 1,2-dodecanediol and of polyglycerol containing 4 glycerol units | 5 g |
| Colorings, preservatives, perfume qs | |
| Lactic acid | 1 g |
| Triethanolamine qs pH = 5 | |
| Water | qsp 100 g |

Example 5

| FOAM BATH | |
|---|---|
| Compound of Example I | 30 g |
| Xanthan gum sold under the trade name of KELTROL T by the KELCO company | 1 g |
| Amido-alkylbetaine of $C_{11}$—$C_{17}$ fatty acids associated with a monoglyceride sold at a 30% concentration of AS under the trade name TEGOBETAINE HS by the GOLDSCHMIDT company | 3 g AS |
| Colorings, preservatives, perfume qs | |
| Triethanolamine qs pH = 6 | |
| Water | qsp 100 g |

Example 6

| FOAM BATH | |
|---|---|
| Compound of Example VII | 25 g |
| Sodium salt of polyacrylamido-methylpropane sulphonic acid sold at a 15% concentration of AS under the trade name COSMEDIA POLYMER HSP | |

| FOAM BATH -continued | |
|---|---|
| 1180 by the HENKEL company | 2 g AS |
| Colorings, preservatives, perfume qs | |
| Hydrochloric acid qs pH = 5 | |
| Water | qsp 100 g |

Example 7

| SHAMPOO | |
|---|---|
| Compound of Example VIII | 12 g |
| Sodium alkyl ($C_{12-14}$) ether sulphate, oxyethylenated with 2.2 moles of ethylene oxide | 8 g |
| Coconut diethanolamides | 2 g |
| Colourings, preservatives, perfume qs | |
| Triethanolamine qs pH = 7 | |
| Water | qsp 100 g |

Example 8

| SHAMPOO | |
|---|---|
| Compound of Example III | 15 g |
| Alkyl ether of 1,2-dodecanediol and of polyglycerol containing 4 glycerol units | 5 g |
| Tartaric acid | 1 g |
| Triethanolamine qs pH = 5 | |
| Water | qsp 100 g |

Example 9

| FOAM BATH | |
|---|---|
| Compound of Example I | 20 g |
| 1,2-dodecanediol | 1 g |
| Colouring, preservative, perfume qs | |
| Citric acid | 1 g |
| NaOH qs pH = 4 | |
| Water | qsp 100 g |

Example 10

| FOAM BATH | |
|---|---|
| Compound of Example I | 10 g |
| Sodium $C_{12}$—$C_{14}$ alkyl ether sulphate, oxyethylenated with 2.2 moles of ethylene oxide | 10 g |
| Coconut diethanolamides | 2 g |
| Citric acid | 1 g |
| NaOH qs pH = 5 | |
| Water | qsp 100 g |

Example 11

| MAKE-UP REMOVAL LOTION | |
|---|---|
| Compound of Example V | 1 g |
| Copolymer of ethylene oxide/ propylene oxide of about 2,400 MW sold under the trade name PLURONIC L 62 by the BASF WYANDOTTE company | 0.5 g |
| Preservative, perfume, colouring qs | |

| MAKE-UP REMOVAL LOTION -continued | |
|---|---|
| Lactic acid | 0.5 g |
| NaOH qs pH = 5.5 | |
| Water | qsp 100 g |

Example 12

| FOAMING MAKE-UP REMOVAL MILK | |
|---|---|
| Compound of Example I | 5 g |
| Sorbitan monolaurate polyoxy-ethylenated with 20 moles of ethylene oxide, sold under the trade name TWEEN 20 by the ATLAS company | 5 g |
| Mixture of cetyl/stearyl alcohols and of cetyl/stearyl alcohols oxyethylenated with 33 moles of ethylene oxide, sold under the trade name SINNOWAX AO by the HENKEL company | 2 g |
| Glycerin | 0.6 g |
| Preservative, perfume qs | |
| Lactic acid | 0.5 g |
| NaOH qs pH = 6 | |
| Water | qsp 100 g |

We claim:

1. An aqueous foaming cosmetic composition for cleaning the hair or skin comprising at least one surfactant oligomer of formula (I):

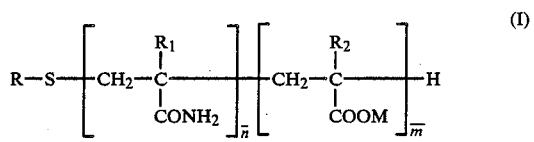

wherein
R represents a linear $C_{10}$ to $C_{18}$ hydrocarbon radical,
$R_1$ and $R_2$, each independently, represent hydrogen or methyl,
$\overline{n}$ represents an average statistical value of 10 to 35,
$\overline{m}$ represents 0 or an average statistical value equal to or less than 5 and, when $\overline{m}$ is other than 0, the ratio $\overline{m}/\overline{n}$ is less than or equal to 0.25,
M represents H, Na, K or, as an ammonium group, $NH_4$, 2-ammonio-2-methyl-1-propanol, 2-ammonio-2-methyl-1,3-propanediol, trimethylhydroxyethylammonium or triethanolamine and,
as an acidifying agent, a $C_2$-$C_6$ carboxylic acid present in an amount such that said composition has a pH ranging from 3 to 7.

2. The composition of claim 1 wherein R represents dodecyl, $R_1$ represents hydrogen or methyl, $\overline{n}$ represents an average statistical value of 10 to 30 and $\overline{m}$ represents 0.

3. The composition of claim 1 wherein R is $C_{12}$-$C_{18}$ alkyl, $\overline{n}$ represents an average statistical value of 10 to 30, $\overline{m}$ represents 0 or an average statistical value of 5, $R_1$ represents hydrogen or methyl and $R_2$ represents methyl.

4. The composition of claim 1 wherein R represents stearyl, $R_1$ represents hydrogen, $R_2$ represents methyl, $\overline{n}$ represents an average statistical value of 20 and $\overline{m}$ represents an average statistical value of 5.

5. The composition of claims 1 in the form of a shampoo or shower product containing from 5 to 25 weight percent of the compound of formula (I).

6. The composition of claim 1 in the form of a foam bath containing from 10 to 95 weight percent of the compound of formula (I).

7. The composition of claim 1 in the form of a makeup removal composition containing from 0.5 to 5 weight percent of the compound of formula (I).

8. The composition of claim 1 in the form of an aqueous solution or an aqueous gel.

9. The composition of claim 1 which also includes another surfactant selected from the group consisting of an anionic, nonionic, amphoteric and zwitterionic surfactant, and a foam stabilizer.

10. The composition of claim 1 which also includes at least one adjuvant selected from a natural polymer, a synthetic polymer, a thickener, an opacifier, an oil, a wax, a protein, an amino acid, a preservative, a coloring agent and a perfume.

* * * * *